US008504146B2

(12) United States Patent
Joshi et al.

(10) Patent No.: US 8,504,146 B2
(45) Date of Patent: Aug. 6, 2013

(54) MULTI-CHANNEL MYOELECTRICAL CONTROL USING SINGLE MUSCLE

(75) Inventors: Sanjay S. Joshi, Davis, CA (US); Anthony S. Wexler, Davis, CA (US); Claudia Perez-Maldonado, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 1164 days.

(21) Appl. No.: 12/163,919

(22) Filed: Jun. 27, 2008

(65) Prior Publication Data

US 2009/0005700 A1  Jan. 1, 2009

Related U.S. Application Data

(60) Provisional application No. 60/947,283, filed on Jun. 29, 2007.

(51) Int. Cl.
*A61B 5/04* (2006.01)
*G09G 5/00* (2006.01)
*G09G 5/08* (2006.01)
*G06F 3/033* (2006.01)

(52) U.S. Cl.
USPC ............ 600/546; 345/156; 345/157; 345/158

(58) Field of Classification Search
USPC .................... 600/546; 345/158–160; 623/25
See application file for complete search history.

(56) References Cited

U.S. PATENT DOCUMENTS

6,636,763 B1 * 10/2003 Junker et al. ............... 600/545
2001/0056225 A1 * 12/2001 DeVito .......................... 600/300

OTHER PUBLICATIONS

Barrero, V.; Grisales, E.V.; Rosas, F.; Sanchez, C.; Leon, J. "Design and Implementation of an intelligent interface for myoelectric controlled prosthesis." Papers from 23rd Annual International Conference of the IEEE Engineering in Medicine and Biology Society. Oct. 2001. Instanbul, Turkey.*

* cited by examiner

*Primary Examiner* — Jeffrey G Hoekstra
*Assistant Examiner* — Megan Leedy
(74) *Attorney, Agent, or Firm* — Park, Vaughan, Fleming & Dowler LLP; Fang Chen (57) ABSTRACT

One embodiment of the present invention provides a system that generates multiple control signals from an electromyographic (EMG) signal produced by a single muscle. During operation, the system obtains an EMG signal from a single muscle of a subject. The system then processes the EMG signal to generate two or more independent control signals from the single muscle.

32 Claims, 5 Drawing Sheets

EMG-SIGNAL MEASURING AND PROCESSING SYSTEM 100

MULTI-CHANNEL MYOELECTRICAL CONTROL USING SINGLE MUSCLE

RELATED APPLICATION

This application hereby claims priority under 35 U.S.C. §119 to U.S. Provisional Patent Application No. 60/947,283, filed on 29 Jun. 2007, entitled "MULTIPLE CHANNEL MYOELECTRICAL CONTROL USING SINGLE MUSCLE," by the same inventors, which is incorporated by reference herein.

BACKGROUND

1. Field of the Invention

The present invention generally relates to techniques for using electrical signals generated by the human body as a means of control. More specifically, the present invention relates to a method and an apparatus for using electrical signals generated by single muscle contractions to control multiple aspects of a single device or multiple devices.

2. Related Art

With more than 250,000 people living with spinal cord injuries in the United States alone, there has always been strong motivation to develop systems that can improve the independence and quality of life of people with such injuries. Individuals who are paralyzed or have other conditions which cause severely impaired mobility often need power wheelchairs to move around. Currently available power wheelchairs are typically controlled by manipulating a joystick controller with one hand. However, individuals with severe spinal injuries cannot use their hands, and thus cannot use these joystick-based wheelchairs.

Several alternative techniques based on other viable body functions have been developed for controlling power wheelchairs without using the hand. These viable body functions can include, but are not limited to, head movement, voice, tongue, eye-gaze, and breathing. However, while obviating the use of a hand to control the wheelchair, systems based on these body functions can interfere with normal body functions and routine activities.

Systems based on electrical brain signals (brain-computer interfaces or "BCIs") provide another exciting form of human-machine interface for mobility-impaired individuals. In particular, for patients without consistent command of body muscles, BCIs provide one of the only meaningful solutions for achieving control of their environment. However, surface electroencephalographic (EEG) BCIs require electrode placement over a large part of the scalp, and direct recordings from the brain cortex require an invasive surgical procedure to implant the electrodes into the cortex. Hence, for those patients with consistent control of at least some muscles, systems based on electrical brain signals may not represent a preferable mode for controlling a power wheelchair.

Alternatively, electromyographic (EMG) systems based on electrical signals generated by muscle contractions ("EMG signals" hereafter) have been used to control moving objects, such as power wheelchairs, or video-game controllers. These EMG-based systems require no surgical electrode placement, and electrodes may be placed over only a small localized area of the head. Unfortunately, current EMG-based systems use one muscle for each control channel, and hence require multiple muscles to control multiple aspects of an object, such as navigating a power wheelchair. This requirement necessitates extensive wiring on a subject, imposes requirement on the subject to simultaneously control multiple muscles, and interferes with the normal functions of these muscles.

Hence, what is needed is a method and a system for controlling multiple objects or multiple aspects of an object using EMG signals without the above-described problems.

SUMMARY

One embodiment of the present invention provides a system that generates multiple control signals from an electromyographic (EMG) signal produced by a single muscle. During operation, the system obtains an EMG signal from a single muscle of a subject. The system then processes the EMG signal to generate two or more independent control signals from the single muscle.

In a variation on this embodiment, the system generates the two or more independent control signals by filtering the EMG signal using a first band-pass filter to obtain a first signal channel comprising a first frequency band. The system additionally filters the EMG signal using a second band-pass filter to obtain a second signal channel comprising a second frequency band. Note that the first frequency band and the second frequency band are substantially non-overlapping, and the first signal channel and the second signal channel are substantially uncorrelated with each other. Next, the system generates first independent control signal and second independent control signal from the first signal channel and the second signal channel.

In a further variation, the system filters the EMG signal using a third band-pass filter to obtain a third signal channel comprising a third frequency band. Note that the third frequency band is substantially non-overlapping with the first and the second frequency band, and the third signal channel is substantially uncorrelated with the first and the second signal channels. The system then generates a third independent control signal from the third signal channel.

In a further variation, the system generates the first, the second, and the third independent control signals from the first, the second, and the third signal channels by: generating the first independent control signal by measuring a first power contained in the first signal channel; generating the second independent control signal by measuring a second power contained in the second signal channel; and generating the third independent control signal by measuring a third power contained in the third signal channel.

In a further variation, the system measures the power contained in a respective signal channel by: obtaining a respective power-spectral signal from the respective signal channel; and computing the respective power by integrating the respective time or frequency signal channel over its respective range of frequencies.

In a further variation, prior to processing the EMG signal to generate the two or more independent control signals, the system selects the first, the second, and the third frequency bands based on a calibration EMG signal produced by the single muscle.

In a further variation, the system selects the first, the second, and the third frequency bands based on the calibration EMG signal by: obtaining the calibration EMG signal from the single muscle; performing a frequency analysis on the calibration EMG signal to obtain a power spectrum; dividing the power spectrum into a set of frequency bands; and selecting the first, the second, and the third frequency bands from the set of frequency bands, such that the power data within the first, the second, and the third frequency bands substantially uncorrelated to each other.

In a further variation, the system selects the first, the second, and the third frequency bands by first computing a correlation coefficient indicating an amount of correlation between the power data of the pair of frequency bands for each pair of frequency bands within the set of frequency bands. The system then selects three frequency bands from the set of frequency bands, wherein a computed correlation coefficient associated with the power data of any two of the three frequency bands is below a predetermined threshold value.

In a further variation, the system obtains the calibration EMG signal by recording multiple EMG signals from the same single muscle over multiple recording sessions and averaging the multiple EMG signals to obtain the calibration EMG signal.

In a further variation, the frequency analysis involves using a Fourier transform.

In a variation on this embodiment, the system uses the two or more independent control signals to simultaneously control multiple objects or multiple aspects of a single object.

In a further variation on this embodiment, the simultaneously controlled objects can include multiple devices; multiple objects; multiple aspects of an object; multiple muscles; and a combination of the above.

In a further variation, the system controls multiple aspects of an object by using two independent control signals to control the (X, Y) coordinates for two-dimensional (2D) movement of the object.

In a further variation, the system uses the two independent control signals to control the 2D motion of the object by performing a mapping from the two independent control signals to the (X, Y) coordinates of the object.

In a variation on this embodiment, the single muscle is an auricularis muscle.

DETAILED DESCRIPTION

The following description is presented to enable any person skilled in the art to make and use the invention, and is provided in the context of a particular application and its requirements. Various modifications to the disclosed embodiments will be readily apparent to those skilled in the art, and the general principles defined herein may be applied to other embodiments and applications without departing from the spirit and scope of the present invention. Thus, the present invention is not limited to the embodiments shown, but is to be accorded the widest scope consistent with the claims.

The data structures and code described in this detailed description are typically stored on a computer-readable storage medium, which may be any device or medium that can store code and/or data for use by a computer system. This includes, but is not limited to, volatile memory, non-volatile memory, magnetic and optical storage devices such as disk drives, magnetic tape, CDs (compact discs), DVDs (digital versatile discs or digital video discs), or other media capable of storing computer-readable media now known or later developed.

Overview

Conventional electromyographic (EMG)-based signal-generating systems produce a single control signal from each muscle based on contractions of the muscle. To provide simultaneous control of multiple objects, these techniques require several sensors to be mounted on several muscles of the subject or a pair of sensors that acquire combined information from all the muscles in their vicinity.

Embodiments of the present invention facilitate using the EMG signals produced by the contractions of a single muscle to control multiple aspects of one or more devices. More specifically, embodiments of the present invention provide a system that records an EMG signal of a single superficial muscle. The system then processes the EMG signal to produce two or more independent (i.e., uncorrelated) control signals which may be used to simultaneously control multiple actuators, multiple devices/objects, multiple aspects of a device/object, multiple muscles, or a combination of the above.

In some embodiments of the present invention, prior to producing the multiple control signals, the single muscle generating the EMG signal is trained using a biofeedback technique and/or other feedback techniques to facilitate selection of frequency bands within the EMG signal. More specifically, a subject is asked to use single muscle contractions to simultaneously control two or more aspects of an object associated with an objective. Next, the EMG signals generated during the calibration process are collected and subjected to a signal processing operation, which identifies two or more uncorrelated frequency bands within the EMG signals. During a subsequent control-signal-generation process, the system can generate each of multiple independent control signals from a respective filtered EMG signal corresponding to a respective frequency band with uncorrelated power data.

Embodiments of the present invention can also be applied to multiple muscles to simultaneously obtain an even greater number of control signals, wherein each of the multiple muscles is configured to generate one or more independent control signals.

EMG-Signal Processing System Setup

Embodiments of the present invention collect the electrical signals produced by the contractions of a single muscle using, for example, conventional biosignal acquisition techniques (described below). Note that the physiological origin of the EMG signal is well understood in the art, and therefore is not described herein. The collected EMG signals are subsequently processed to produce two or more control signals. Note that these multiple control signals are substantially uncorrelated with each other, and hence can be used to control multiple independent objects.

Figure 1:
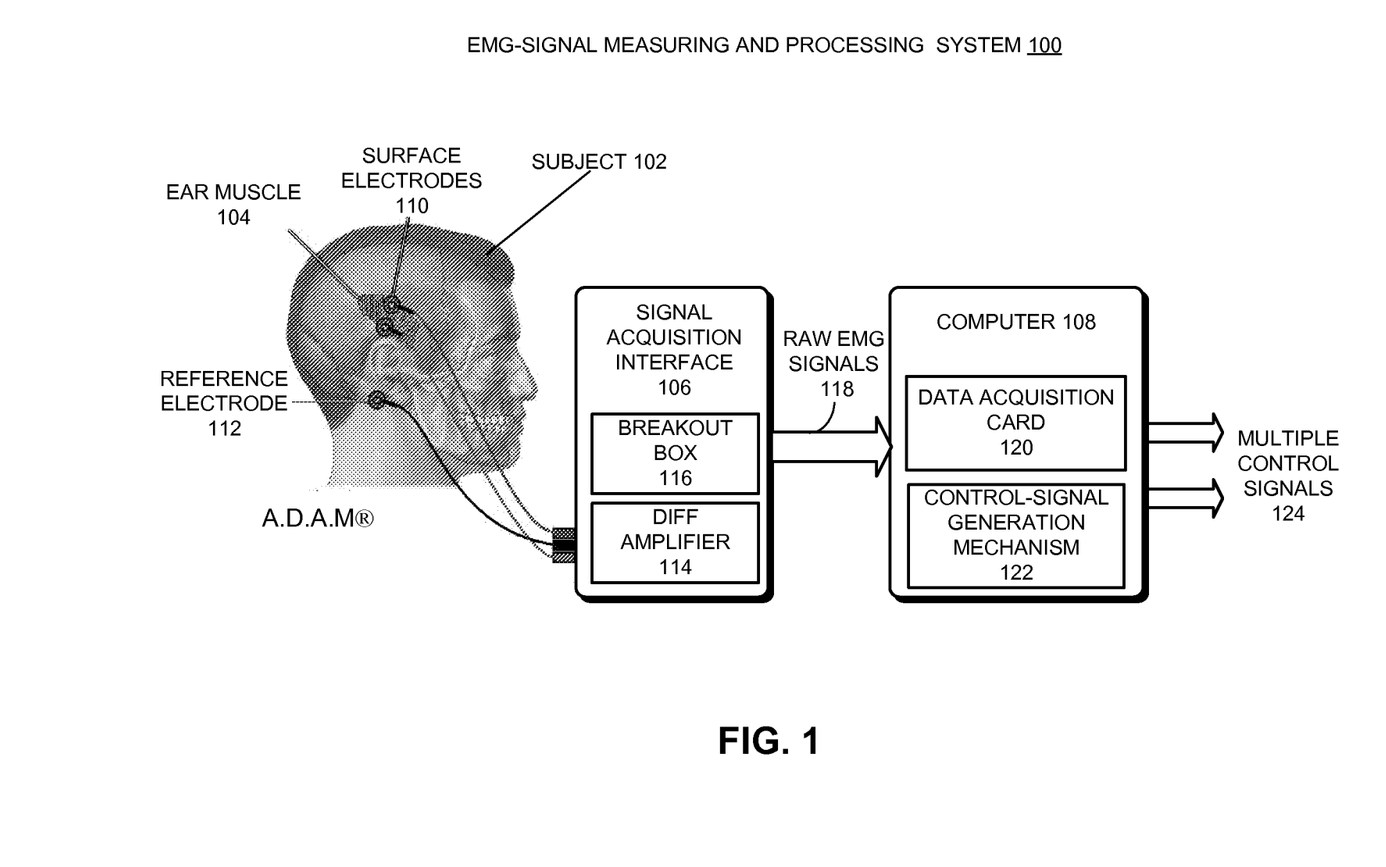
FIG. 1 illustrates an electromyographic (EMG) signal measuring and processing system in accordance with an embodiment of the present invention.

FIG. 1 illustrates an EMG-signal measuring and processing system 100 in accordance with an embodiment of the present invention. As seen in FIG. 1, system 100 includes a subject 102 (the head illustration is borrowed from A.D.A.M.®), which is also the EMG-signal source. In one embodiment, the EMG signal is produced by the contraction of a single muscle of subject 102. In the illustrated example, the single muscle is the auricularis superior muscle 104 which controls the wiggling of an ear (or "ear muscle" hereafter). Note that although the present invention is described in terms of using an ear muscle, the present invention is not meant to be limited to an ear muscle. In other embodiments, the single muscle used to generate the EMG-signal can be the auricularis anterior muscle, the auricularis posterior muscle, another single head muscle, or any other single muscle of subject 102. Note that for a subject impaired by severe spinal cord injuries, the single muscle may be exclusively selected from a head muscle. Also note that using a vestigial muscle such as an auricularis muscle allows the other facial muscles to continue performing emotional and communicational functions.

System 100 also includes an EMG signal acquisition interface 106, which is coupled between ear muscle 104 and a computer 108. In some embodiments, signal acquisition interface 106 (or acquisition interface 106 hereafter) measures the EMG signals from ear muscle 104, preprocesses the signals, and then transmits the signals into computer 108 for further processing. As illustrated in FIG. 1, acquisition interface 106 receives EMG signals through two surface electrodes 110 attached to ear muscle 104. In one embodiment, the EMG signal generated by ear muscle 104 is measured in a differential mode. For example, two surface electrodes 110 can be adhered to the skin from opposite ends of ear muscle 104 (shown above the subject's ear). Additionally, a reference electrode 112 is adhered to the mastoid process to provide a reference potential for the differential signals.

In some embodiments of the present invention, setting up the surface electrodes on the ear muscle requires a trial-and-error adjustment. For example, one embodiment measures the impedance between each of the surface electrodes and the reference electrode. If the measurement is greater than a predetermined value, e.g., 5 kΩ, the electrodes are moved a little and some pressure is added to see if the impedance can be improved. If the impedance cannot be lowered this way, the electrodes are removed; the skin and the electrodes are cleaned with alcohol, and the electrodes are reattached to the skin. The impedance measurement is then repeated, and the same process is followed until the impedance values are below the predetermined value.

In some embodiments, acquisition interface 106 includes a differential amplifier 114 which amplifies the amplitude of raw EMG signals received from the differential electrodes 110 and reference electrode 112. In some embodiments, acquisition interface 106 can include additional preprocessing components for conditioning the raw EMG signal. Acquisition interface 106 can also include a breakout box 116, which facilitates coupling the preprocessed raw EMG signals to a standard electrical connector (such as a D-sub), so that the raw EMG signals can be coupled to computer 108 through a standard I/O port, such as a parallel port, a serial port, a USB port, or an audio port.

Computer 108 receives preprocessed raw EMG signals 118 from acquisition interface 106. In some embodiments, computer 108 includes a data acquisition (DAQ) card 120 which can be inserted in a slot (e.g., PCI, ISA) in the motherboard of computer 108. Note that such a DAQ card often includes multiple signal-processing components for processing the EMG signals. These signal-processing components can include, but are not limited to, an analog-to-digital converter (ADC), a digital-to-analog converter (DAC), a TTL-IO, high speed timers, and a microcontroller. In some embodiments of the present invention, one or more of these components can be implemented on acquisition interface 106 outside computer 108. Note that the above-mentioned data acquisition hardware is conventional, and hence is not described in more detail.

Computer 108 also includes a control-signal generation mechanism 122, which performs digital signal processing operations on the sampled and digitized EMG signals to generate two or more channels of independent control signals 124. These control signals can then be used to simultaneously control multiple objects, or multiple aspects of a single object. In some embodiments, control-signal generation mechanism 122 generates multiple control signals 124 using two or more band-pass filters, wherein each band-pass filter produces a filtered signal having a specific frequency range determined by the respective band-pass filter. The multiple filtered signals corresponding to different frequency ranges are then used as the multiple channels of control signals. We describe embodiments of control-signal generation mechanism 122 in more detail below.

Note that although the present invention is described in terms of using a differential signal-measuring mode, the present invention is not meant to be limited to differential signal collection. In general, the present invention can be used with any type of signal measurement configuration.

Processing an EMG Signal to Generate Multiple Control Signals

Figure 2:
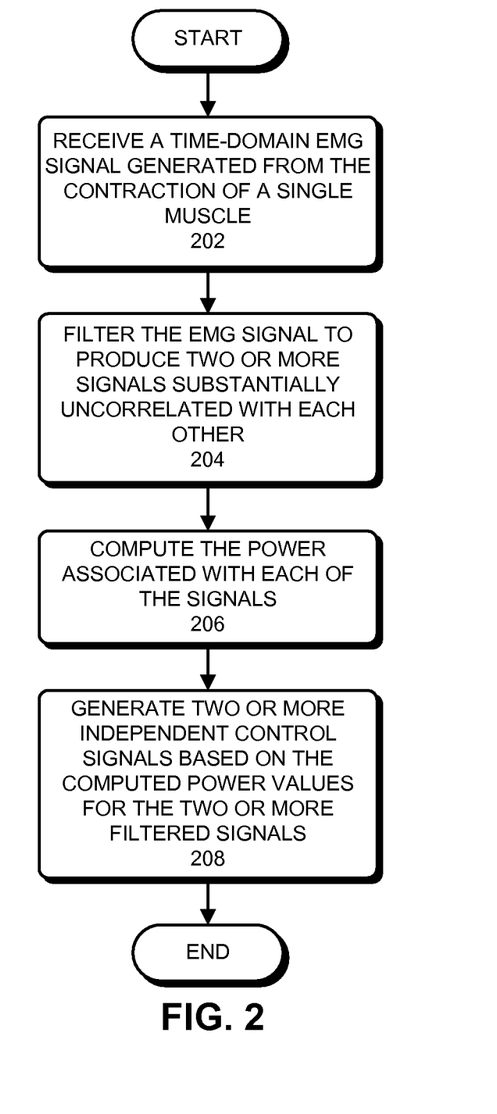
FIG. 2 presents a flowchart illustrating a process for producing multiple independent control signals from an EMG signal generated from a single muscle in accordance with an embodiment of the present invention.

FIG. 2 presents a flowchart illustrating a process for producing multiple independent control signals from an EMG signal generated from a single muscle in accordance with an embodiment of the present invention.

During operation, the system receives a time-domain EMG signal generated from the contraction of a single muscle (step 202). In some embodiments, the time-domain EMG signal is a sampled and digitized time series signal.

Next, the system filters the received EMG signal to produce two or more signals which contain specific frequencies, wherein the two or more signals are substantially uncorrelated to each other (step 204). In other words, each of the filtered signals comprises at least one unique frequency range. In some embodiments, the system uses two or more band-pass filters to filter the received EMG signal to produce the filtered signals which contain only non-overlapping frequency bands. In this embodiment, each band-pass filter specifies a unique and predetermined frequency band. For example, 41-60 Hz and 61-80 Hz band-pass filters can be used to generate a first signal containing mostly frequencies from 41-60 Hz and a second signal containing mostly frequencies from 61-80 Hz.

Note that filtered signals which are associated with arbitrarily non-overlapping frequency bands are not necessarily uncorrelated signals. In some embodiments of the present invention, the predetermined frequency bands are identified beforehand through a calibration process performed on the same single muscle of the same subject. Note that the calibration process is ideally performed for each subject in order to customize the predetermined frequency bands for each subject. This calibration process for identifying the predetermined frequency bands is described in more detail below in conjunction with FIGS. 3 and 4.

After generating the two or more uncorrelated signals from the EMG signal, the system next computes the power associated with each of the signals (step 206). In one embodiment, obtaining the power contained in a filtered signal involves integrating over the entire frequency range of the filtered signal to obtain the total power for the respective filtered signal. Note that the computed power value corresponds to the energy generated by the single muscle in the respective range of frequencies.

The system then generates two or more independent control signals based on the computed power values for the two or more filtered signals (step 208). Note that the system can generate application specific control signals by using a mapping. For example, two independent control signals can be used to control two-dimensional (2D) motion of a cursor on a computer screen. In this example, the mapping maps the power values associated with a first and a second frequency band to the (X,Y) coordinates representing the position of the cursor. Consequently, as the subject continuously contracts the single muscle, a continuous control of the cursor movement can be realized.

Hence, the above-described process generates multiple independent control signals from the EMG signal produced by a single muscle, wherein each independent control signal is used to control one of multiple aspects of an object, or multiple objects.

Identifying Independent Control Channels within an EMG Signal

In some embodiments of the present invention, the predetermined frequency ranges used to generate the uncorrelated control signals are determined based on an offline calibration process performed on the same subject. More specifically, the calibration process is used to analyze frequency bands of a given bandwidth (e.g., 20 Hz) over the entire bandwidth of the EMG signal generated by the single muscle to identify the power data within those frequency bands that are substantially uncorrelated. If such frequency bands are found, they can be used to select the predetermined frequency ranges, which are then used to generate each of the control signals. Note that because the EMG signals generated by each subject are generally unique, the independent frequency bands identified through this calibration process are customized specifically for each subject.

Figure 3:
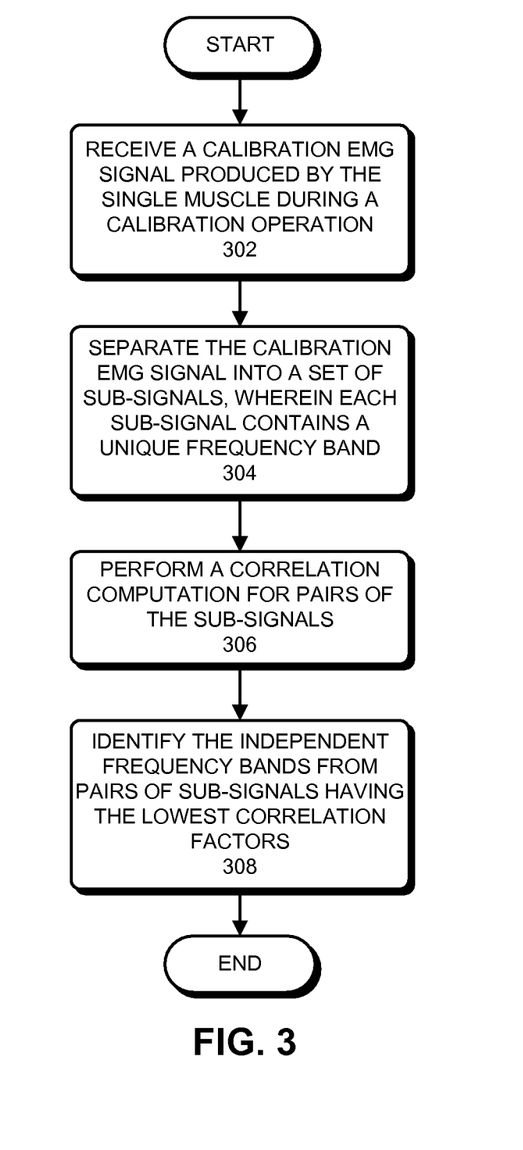
FIG. 3 presents a flowchart illustrating a process for identifying independent frequency bands within a calibration EMG signal in accordance with an embodiment of the present invention.

FIG. 3 presents a flowchart illustrating a process for identifying independent frequency bands within a calibration EMG signal in accordance with an embodiment of the present invention.

During operation, the system receives the calibration EMG signal ("calibration signal" hereafter) produced by the single muscle of the subject, wherein the calibration signal is produced during a calibration operation performed on the subject to facilitate selection of frequency bands whose power data is substantially uncorrelated (step 302). The calibration operation for generating the calibration signal is described below in more detail in conjunction with FIG. 4. Note that the calibration signal contains a range of frequencies.

The system then separates the calibration signal into a set of sub-signals, wherein each sub-signal contains a unique frequency band (step 304). In some embodiments, the system separates the calibration signal into the sub-signals by first performing a frequency analysis on the calibration signal to obtain the power spectrum. For example, the system can perform a Fourier transform on the calibration signal. Next, the system divides the power spectrum into a set of frequency bands, wherein each frequency band corresponds to one of the sub-signals. In one embodiment, the system divides the power spectrum into a set of substantially equal-bandwidth frequency bands, wherein the width of the bands is predetermined. Note that choosing the width of the bands typically involves considering trade-offs between a number of factors. For example, if the bands are too wide, correlation between bands increases while sensitivity decreases. On the other hand, if the bands are too narrow sensitivity increases. In some embodiments, the width of the bands is chosen to be approximately 20 Hz.

In some embodiments of the present invention, the system can separate the calibration signal into the sub-signals directly in the time domain by passing the calibration signal through a set of band-pass filters, where each band-pass filter generates a sub-signal having a unique frequency band. Note that because each sub-signal is characterized by a unique frequency band, we refer to each of the sub-signals by its corresponding frequency band below.

After separating the calibration signal into the set of sub-signals associated with the different frequency bands, the system performs a correlation computation for each pair of the frequency bands (step 306). In some embodiments, the system first computes the power contained within each of the frequency bands. Next, for each frequency band, the system computes a correlation coefficient R between the frequency band and each of the other frequency bands, wherein the correlation coefficient indicates an amount of correlation between the power values associated with the pair of frequency bands. Note that this correlation computation effectively creates a correlation matrix for the set of frequency bands.

Next, the system identifies the independent frequency bands from pairs of frequency bands having the lowest correlation coefficients, for example all frequency pairs with R<0.1 (step 308). In some embodiments, if two independent frequency bands are needed, the system can simply choose a pair of frequency bands associated with the lowest overall correlation coefficient (which is also below the threshold R<0.1). In some embodiments, if three independent control signals need to be generated, the system can choose three frequency bands, such that the relative correlation among the three bands is below the threshold. In some embodiments, the independent frequency bands can be selected based on both low correlation coefficients and a preference for frequency bands in the low frequency range, for example below 100 Hz.

After identifying the independent frequency bands, the system can use these frequency bands to design band-pass filters for processing normal EMG signals collected from the subject.

Figure 4:
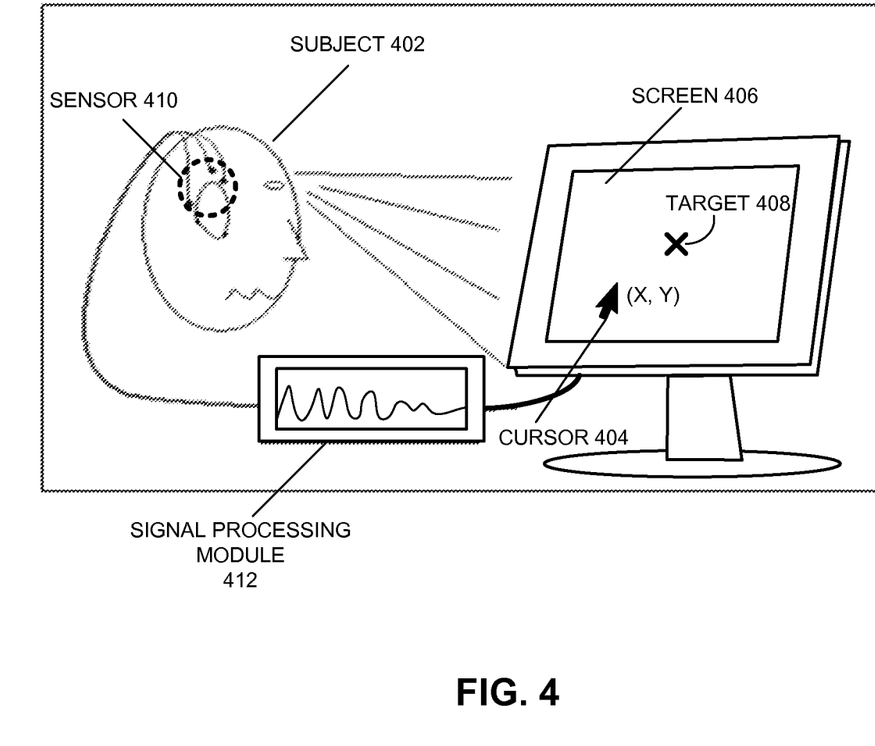
FIG. 4 illustrates a calibration operation performed on a subject to generate the above-mentioned calibration EMG signal in accordance with an embodiment of the present invention.

FIG. 4 illustrates a calibration operation performed on a subject 402 to generate the above-mentioned calibration EMG signal in accordance with an embodiment of the present invention.

As illustrated in FIG. 4, subject 402 uses the contractions of a single ear muscle to control the position of a cursor 404 displayed on a screen 406 and attempts to hit a target 408 on screen 406. Through each contraction of the ear muscle, subject 402 generates an EMG signal which is measured by a sensor 410 mounted on the skin proximate to the ear muscle. Note that sensor 410 can include multiple electrodes. The EMG signal collected by sensor 410 is coupled to a signal processing module 412 which processes the EMG signal to generate two control signals. Signal processing module 412 also performs a mapping to generate the (X,Y) coordinates of cursor 404 from the two control signals.

In some embodiments, to generate the two control signals from the EMG signal, the system selects two frequency bands within the frequency spectrum of the EMG signal. Note that at this stage, the system has no knowledge in regard to which frequency bands in the EMG signal are uncorrelated. Consequently, these two frequency bands can be arbitrarily selected or, alternatively, based on an educated guess. For example, frequency bands in the low frequency range (<100 Hz) may be preferred for the reasons described above. Upon selecting the two frequency bands, the system can process an EMG signal produced by each contraction using the process described in conjunction with FIG. 2, which eventually maps the two control signals to the (X,Y) coordinates of cursor 404.

Note that the calibration operation illustrated in FIG. 4 involves a simple visual feedback process to control how the subject adjusts the muscle contractions to achieve the desired objective. More specifically, subject 402 sees the entire screen 406 during the calibration operation. After each contraction, if the generated cursor position $(X_1, Y_1)$ fails to hit target 408, subject 402 adjusts the muscle contraction to causes cursor 404 to move to a new position $(X_2, Y_2)$. This time, if the new position $(X_2, Y_2)$ still fails to hit target 408, subject 402 continues to adjust the muscle contraction to cause cursor 404 to move to a different position $(X_3, Y_3)$. Subject 402 repeats this feedback-loop operation until cursor 404 hits target 408 by way of muscle contraction, and then keeps contracting the muscle in the same manner.

In some embodiments of the present invention, multiple target positions may be used, wherein for each position of target 408, subject 402 performs a set of contractions. In some embodiments, these contractions may be separated into multiple sessions. For example, for each target position, one session of 20 contractions may be performed continuously with short breaks, and a total of 10 sessions may be carried out which are separated by some rest time between sessions. Next, the position of target is changed, and another set of contraction sessions are performed by subject 402 while attempting to hit the target at the new position.

Note that during the above-described calibration operation, a large number of calibration EMG signals corresponding to a large number of muscle contractions are collected. In one embodiment of the present invention, each of these calibration EMG signals is converted into a frequency spectrum and divided into frequency bands. The power-spectral signal for each frequency band is then computed. Next, for each frequency band, the power-spectral signals over all calibration EMG signals (i.e., calibration EMG signals associated with multiple target positions) are averaged. Consequently, the subsequent correlation computation for each pair of frequency bands (i.e., step 308 in FIG. 3) is performed on the averaged-power-spectral signals over a large number of calibration EMG signals associated with a large number of muscle contractions.

Note that although the calibration operation illustrated in FIG. 4 is directed to generating two independent control signals, other calibration operations can be performed to generate more control signals. For example, a 3D display of cursor and target in a 3D display environment may be used to train three or more control channels.

Also note that from a physiological perspective, the above-described calibration process allows precisely coordination by the brain of the motor neurons controlling the single muscle contraction to fire at specific rates, therefore generate the power in the specific frequency bands. Consequently, the calibration process facilitates selection of frequency bands within the EMG signal. Although the independent frequency bands and the power range associated with each band may vary from subject to subject and the position of the sensor, if the sensor location is fixed and the subject has been properly trained, the subject is capable of generating EMG signals with a repeatable waveform and amplitude.

Application

One application of the multiple independent control signals extracted from the EMG signals of a single muscle is to control the movement of an electric-power-wheelchair (EPW) to help patients who experience difficulty using a regular joystick controller.

Figure 5:
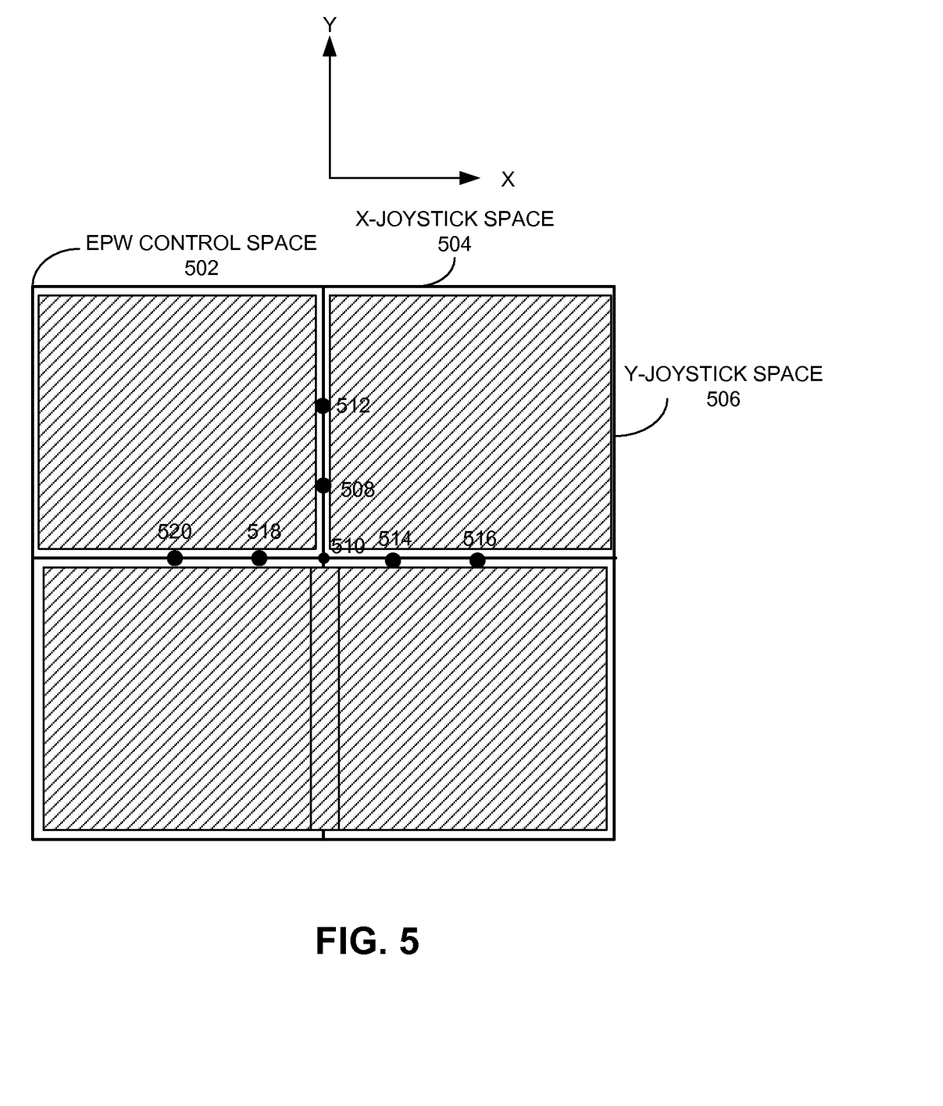
FIG. 5 illustrates an exemplary mapping scheme between two EMG control signals and the movement of the Electric Power Wheelchair (EPW) in accordance with an embodiment of the present invention.

Using the above-described procedures, two 20 Hz frequency bands in the low end of the frequency spectrum and having a correlation coefficient <0.1 are extracted from the EMG signals to generate two independent control signals for the EPW. FIG. 5 illustrates an exemplary mapping scheme between the two EMG control signals and the movement of the EPW in accordance with an embodiment of the present invention. As illustrated in FIG. 5, the two EMG control signals are mapped onto a 2D-EPW control space 502, which can be decomposed into X-joystick space 504 in the horizontal direction and Y-joystick space 506 in the vertical direction. Note that the movement of the EPW can be specified by a direction parameter and a speed parameter. In this example, the positive Y-direction corresponds to moving forward, the negative Y-direction corresponds to moving backward, the positive X-direction corresponds to turning right, the negative X-direction corresponds to turning left. Furthermore, the distance from the center of the control space represents the speed.

Note that if the two control signals are mapped to location 508 directly above origin 510, the EPW moves forward at a specific speed, and if they are mapped to location 512 further above origin 510, the EPW moves forward at a faster speed. On the other hand, if the two control signals are mapped to location 514 directly to the right of origin 510, the EPW turns to the right at a specific speed, and if they are mapped to location 516 further to the right of origin 510, the EPW turns to the right at a faster speed. Similarly, if the two control signals are mapped to location 518 directly to the left of origin 510, the EPW turns to the left at a specific speed, and if they are mapped to location 520 further to the left of origin 510, the EPW turns to the left at a faster speed. Note that control space 502 also includes forbidden zones which are represented by the shaded areas. For example, moving backward or turning in an arc may not be allowed. If the two control signals are mapped into a forbidden zone, no action will occur to the EPW. Note that the mapping described herein is for demonstration purposes only. Other mapping schemes between the two control signals and the EPW movements can be readily designed and implemented.

Also note that the application of multiple independent control signals extracted from the EMG signals of a single muscle is not limited to controlling EPWs. Many other applications for these control signals can also be found, for example, in gaming controls.

The foregoing descriptions of embodiments of the present invention have been presented only for purposes of illustration and description. They are not intended to be exhaustive or to limit the present invention to the forms disclosed. Accordingly, many modifications and variations will be apparent to practitioners skilled in the art. Additionally, the above disclosure is not intended to limit the present invention. The scope of the present invention is defined by the appended claims.

What is claimed is:

1. A method for generating multiple control signals from an electromyographic (EMG) signal produced by a muscle, comprising:

obtaining an EMG signal from a single EMG sensor which is placed on a subject to measure contractions of a single muscle of the subject, wherein the single EMG sensor can include multiple electrodes; and processing, by computer, the EMG signal to generate two or more control signals from the measured contractions of the single muscle, wherein the two or more control signals are generated simultaneously, and wherein the two or more control signals are independently controllable by the subject.

2. The method of claim 1, wherein processing the EMG signal to generate the two or more control signals involves:
filtering the EMG signal using a first band-pass filter to obtain a first signal channel comprising a first frequency band, wherein the first signal channel measures a contribution in the first frequency band of the measured contractions of the single muscle;
filtering the EMG signal using a second band-pass filter to obtain a second signal channel comprising a second frequency band, wherein the second signal channel measures a contribution in the second frequency band of the measured contractions of the single muscle,
wherein the first frequency band and the second frequency band are substantially non-overlapping; and
wherein the first signal channel and the second signal channel are substantially uncorrelated with each other; and
generating a first control signal and a second control signal from the first signal channel and the second signal channel.

3. The method of claim 2, wherein the method further comprises:
filtering the EMG signal using a third band-pass filter to obtain a third signal channel comprising a third frequency band,
wherein the third frequency band is substantially non-overlapping with the first and the second frequency band; and
wherein the third signal channel is substantially uncorrelated with the first and the second signal channels; and
generating a third control signal from the third signal channel.

4. The method of claim 3, wherein generating the first, second, and the third control signals from the first, the second, and the third signal channels involves:
generating the first control signal by measuring a first power contained in the first signal channel;
generating the second control signal by measuring a second power contained in the second signal channel; and
generating the third control signal by measuring a third power contained in the third signal channel.

5. The method of claim 4, wherein measuring the power contained in a respective signal channel involves:
obtaining a respective power-spectral signal from the respective range of frequencies; and
computing the respective power by integrating the respective power spectral signal over the respective range of frequencies.

6. The method of claim 3, wherein prior to processing the EMG signal to generate the two or more control signals, the method further comprises selecting the first, the second, and the third frequency bands based on a calibration EMG signal produced by the single muscle.

7. The method of claim 6, wherein selecting the first, the second, and the third frequency bands based on the calibration EMG signal involves:
obtaining the calibration EMG signal from the single muscle;
performing a frequency analysis on the calibration EMG signal to obtain a power spectrum;
dividing the power spectrum into a set of frequency bands; and
selecting the first, the second, and the third frequency bands from the set of frequency bands, such that the power data within the first, the second, and the third frequency bands are substantially uncorrelated to each other.

8. The method of claim 7, wherein selecting the first, the second, and the third frequency bands involves:
for each pair of frequency bands within the set of frequency bands, computing a correlation coefficient indicating an amount of correlation between the power data of the pair of frequency bands; and
selecting three frequency bands from the set of frequency bands, wherein a computed correlation coefficient associated with the power data of any two of the three frequency bands is below a predetermined threshold value.

9. The method of claim 7, wherein obtaining the calibration EMG signal involves:
recording multiple EMG signals from the same single muscle over multiple recording sessions; and
averaging the multiple EMG signals to obtain the calibration EMG signal.

10. The method of claim 7, wherein the frequency analysis involves using a Fourier transform.

11. The method of claim 1, wherein the method further comprises using the two or more control signals to simultaneously control multiple objects or multiple aspects of a single object.

12. The method of claim 11, wherein the simultaneously controlled objects can include:
multiple devices;
multiple objects;
multiple aspects of an object;
and
a combination of the above.

13. The method of claim 11, wherein using the two or more control signals to simultaneously control multiple aspects of an object involves using two control signals to control the (X, Y) coordinates for two-dimensional (2D) movement of the object.

14. The method of claim 13, wherein using the two control signals to control the 2D motion of the object involves performing a mapping from the two control signals to the (X, Y) coordinates of the object.

15. The method of claim 1, wherein the single muscle is an auricularis muscle.

16. A non-transitory computer-readable storage medium storing instructions that when executed by a computer cause the computer to perform a method for generating multiple control signals from an electromyographic (EMG) signal produced by a muscle, the method comprising:
obtaining an EMG signal from a single EMG sensor which is placed on a subject to measure contractions of a single muscle of the subject, wherein the single EMG sensor can include multiple electrodes; and
processing the EMG signal to generate two or more control signals from the measured contractions of the single muscle, wherein the two or more control signals are generated simultaneously, and wherein the two or more control signals are independently controllable by the subject.

17. The non-transitory computer-readable storage medium of claim 16, wherein processing the EMG signal to generate the two or more control signals involves:
filtering the EMG signal using a first band-pass filter to obtain a first signal channel comprising a first frequency band, wherein the first signal channel measures a contribution in the first frequency band of the measured contractions of the single muscle;

filtering the EMG signal using a second band-pass filter to obtain a second signal channel comprising a second frequency band, wherein the second signal channel measures a contribution in the second frequency band of the measured contractions of the single muscle, wherein the first frequency band and the second frequency band are substantially non-overlapping; and wherein the first signal channel and the second signal channel are substantially uncorrelated with each other; and generating a first control signal and a second control signal from the first signal channel and the second signal channel.

18. The non-transitory computer-readable storage medium of claim 17, wherein the method further comprises:

filtering the EMG signal using a third band-pass filter to obtain a third signal channel comprising a third frequency band, wherein the third frequency band is substantially non-overlapping with the first and the second frequency band; and wherein the third signal channel is substantially uncorrelated with the first and the second signal channels; and generating a third control signal from the third signal channel.

19. The non-transitory computer-readable storage medium of claim 18, wherein generating the first, the second, and the third control signals from the first, the second, and the third signal channels involves:

generating the first control signal by measuring a first power contained in the first signal channel;

generating the second control signal by measuring a second power contained in the second signal channel; and generating the third control signal by measuring a third power contained in the third signal channel.

20. The non-transitory computer-readable storage medium of claim 19, wherein measuring the power contained in a respective signal channel involves:

obtaining a respective power spectral signal from the respective range of frequencies; and computing the respective power by integrating the respective power spectral signal over the respective range of frequencies.

21. The non-transitory computer-readable storage medium of claim 18, wherein prior to processing the EMG signal to generate the two or more control signals, the method further comprises selecting the first, the second, and the third frequency bands based on a calibration EMG signal produced by the single muscle.

22. The non-transitory computer-readable storage medium of claim 21, wherein selecting the first, the second, and the third frequency bands based on the calibration EMG signal involves:

obtaining the calibration EMG signal from the single muscle;

performing a frequency analysis on the calibration EMG signal to obtain a power spectrum;

dividing the power spectrum into a set of frequency bands; and selecting the first, the second, and the third frequency bands from the set of frequency bands, such that the power data within the first, the second, and the third frequency bands are substantially uncorrelated to each other.

23. The non-transitory computer-readable storage medium of claim 22, wherein selecting the first, the second, and the third frequency bands involves:

for each pair of frequency bands within the set of frequency bands, computing a correlation coefficient indicating an amount of correlation between the power data of the pair of frequency bands; and selecting three frequency bands from the set of frequency bands, wherein a computed correlation coefficient associated with the power data of any two of the three frequency bands is below a predetermined threshold value.

24. The non-transitory computer-readable storage medium of claim 22, wherein obtaining the calibration EMG signal involves:

recording multiple EMG signals from the same single muscle over multiple recording sessions; and averaging the multiple EMG signals to obtain the calibration EMG signal.

25. The non-transitory computer-readable storage medium of claim 22, wherein the frequency analysis involves using a Fourier transform.

26. The non-transitory computer-readable storage medium of claim 16, wherein the method further comprises using the two or more control signals to simultaneously control multiple objects or multiple aspects of a single object.

27. The non-transitory computer-readable storage medium of claim 26, wherein the simultaneously controlled objects can include:

multiple devices;

multiple objects;

multiple aspects of an object; and a combination of the above.

28. The non-transitory computer-readable storage medium of claim 26, wherein using the two or more control signals to simultaneously control multiple aspects of an object involves using two control signals to control the (X, Y) coordinates for two-dimensional (2D) movement of the object.

29. The non-transitory computer-readable storage medium of claim 28, wherein using the two control signals to control the 2D motion of the object involves performing a mapping from the two control signals to the (X, Y) coordinates of the object.

30. The non-transitory computer-readable storage medium of claim 16, wherein the single muscle is an auricularis muscle.

31. An apparatus that generates multiple control signals from an electromyographic (EMG) signal produced by a muscle, comprising:

a receiving mechanism configured to receive an EMG signal from a single EMG sensor which is placed on a subject to measure contractions of a single muscle of the subject, wherein the single EMG sensor can include multiple electrodes; and a processing mechanism configured to process the EMG signal to generate two or more control signals from the measured contractions of the single muscle, wherein the two or more control signals are generated simultaneously, and wherein the two or more control signals are independently controllable by the subject.

32. The apparatus of claim 31, wherein while processing the EMG signal, the processing mechanism is configured to:

filter the EMG signal using a first band-pass filter to obtain a first signal channel comprising a first frequency band, wherein the first signal channel measures a contribution in the first frequency band of the measured contractions of the single muscle;

filter the EMG signal using a second band-pass filter to obtain a second signal channel comprising a second frequency band, wherein the second signal channel measures a contribution in the second frequency band of the measured contractions of the single muscle,
  wherein the first frequency band and the second frequency band are substantially non-overlapping; and
  wherein the first signal channel and the second signal channel are substantially uncorrelated with each other; and
generate a first control signal and a second control signal from the first signal channel and the second signal channel.

* * * * *